United States Patent
Eury

(10) Patent No.: US 9,981,103 B2
(45) Date of Patent: May 29, 2018

(54) SEALING CUSHION HAVING ANGLED SEALING FLAP

(71) Applicant: KONINKLIJKE PHILIPS N.V., Eindhoven (NL)

(72) Inventor: Matthew Paul Eury, Latrobe, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 241 days.

(21) Appl. No.: 14/406,610

(22) PCT Filed: May 28, 2013

(86) PCT No.: PCT/IB2013/054408
§ 371 (c)(1),
(2) Date: Dec. 9, 2014

(87) PCT Pub. No.: WO2013/186654
PCT Pub. Date: Dec. 19, 2013

(65) Prior Publication Data
US 2015/0151067 A1  Jun. 4, 2015

Related U.S. Application Data

(60) Provisional application No. 61/658,956, filed on Jun. 13, 2012.

(51) Int. Cl.
*A61M 16/06* (2006.01)
*A61M 16/00* (2006.01)

(52) U.S. Cl.
CPC .... *A61M 16/0622* (2014.02); *A61M 16/0057* (2013.01); *A61M 16/06* (2013.01); *A61M 16/0616* (2014.02); *A61M 16/0633* (2014.02)

(58) Field of Classification Search
CPC ....... A61M 16/06–16/0655; A61M 2016/0661
See application file for complete search history.

(56) References Cited

U.S. PATENT DOCUMENTS

| | | |
|---|---|---|
| 7,640,933 B1 | 1/2010 | Ho |
| 2004/0094157 A1 | 5/2004 | Dantanarayana |
| 2004/0221850 A1 | 11/2004 | Ging |
| 2005/0155604 A1* | 7/2005 | Ging ............... A44B 11/266 128/206.21 |
| 2006/0096598 A1 | 5/2006 | Ho |
| 2009/0032024 A1 | 2/2009 | Burz |
| 2010/0108072 A1 | 5/2010 | D'Souza |
| 2011/0162654 A1 | 7/2011 | Carroll |

FOREIGN PATENT DOCUMENTS

| | | |
|---|---|---|
| WO | WO2010135785 A1 | 12/2010 |
| WO | WO2010139014 A1 | 12/2010 |
| WO | 2012025843 A1 | 3/2012 |
| WO | WO2013027144 A1 | 2/2013 |

* cited by examiner

*Primary Examiner* — Rachel T Sippel
(74) *Attorney, Agent, or Firm* — Michael W. Haas

(57) ABSTRACT

A cushion (26) for a patient interface device includes a support wall portion and a sealing flap (40) extending in inwardly from the support wall portion and toward a longitudinal axis of the cushion. The sealing flap has a distal edge (44) which defines an opening (46) in the sealing flap. The opening extends from the nose bridge to the upper lip and is created by two planes (hinged nearer the upper lip) that intersect at a large angle (e.g., 90 degrees to 150 degrees) near the upper lip.

10 Claims, 9 Drawing Sheets

SEALING CUSHION HAVING ANGLED SEALING FLAP

CROSS-REFERENCE TO RELATED APPLICATIONS

This patent application claims the priority benefit under 35 U.S.C. § 371 of international patent application no. PCT/IB2013/054582, filed Jun. 4, 2013, which claims the priority benefit under 35 U.S.C. § 119(e) of U.S. Provisional Application No. 61/658,956 filed on Jun. 13, 2012, the contents of which are herein incorporated by reference.

BACKGROUND OF THE INVENTION

1. Field of the Invention

The present invention pertains to patient interface devices structured to deliver a flow of breathing gas to a user, and, in particular, to a sealing cushion for a patient interface device that has an angled sealing flap providing an improved fit and seal.

2. Description of the Related Art

There are numerous situations where it is necessary or desirable to deliver a flow of breathing gas non-invasively to the airway of a patient, i.e., without intubating the patient or surgically inserting a tracheal tube into the patient's esophagus. For example, it is known to ventilate a patient using a technique known as non-invasive ventilation. It is also known to deliver positive airway pressure (PAP) therapy to treat certain medical disorders, the most notable of which is OSA. Known PAP therapies include continuous positive airway pressure (CPAP), wherein a constant positive pressure is provided to the airway of the patient in order to splint open the patient's airway, and variable airway pressure, wherein the pressure provided to the airway of the patient is varied with the patient's respiratory cycle. Such therapies are typically provided to the patient at night while the patient is sleeping.

Non-invasive ventilation and pressure support therapies as just described involve the placement of a patient interface device including a mask component having a soft, flexible sealing cushion on the face of a patient. The mask component may be, without limitation, a nasal mask that covers the patient's nose, a nasal/oral mask that covers the patient's nose and mouth, or a full face mask that covers the patient's face. Such patient interface devices may also employ other patient contacting components, such as forehead supports, cheek pads and chin pads. The sealing cushion typically has a support portion coupled to a sealing flap portion, which may integrated together as a single part or that may be separate components that when combined together in the final assembly provide the sealing and support functions. The patient interface device is connected to a gas delivery tube or conduit and interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head.

Patient interface devices used in non-invasive ventilation and pressure support therapies should be comfortable and maintain a robust seal, while at the same time optimizing comfort by avoiding the creation of excessive pressure and/or red marks on the user's face. The sealing flap portion should also conform to the face without excessive bunching and encroaching on the patient's eyes, cheeks, and nostrils.

As used herein, the term "bunching" shall refer to an area where, when the sealing cushion is donned by the user, extra sealing flap length collects and folds/curls over itself, resulting in bunches or folds of sealing flap. Bunching can cause patient annoyance, obstruct the patient's view, partially obstruct the patient's air path, and/or create potential leak paths, any or all of which may ultimately decrease the patient's therapy compliance.

Unfortunately, many current patient interface devices used in non-invasive ventilation and pressure support therapies have sealing problems, create pressure on the face, and/or cause red marks and/or sores. One location where such problems, especially pressure points, frequently occur is on and around the portion of the patient's mouth above the upper lip. The occurrence of these problems may often be attributed to the amount of sealing surface area created by traditional sealing flap geometries. Patients also often complain about traditional sealing flaps partially blocking their nostrils and reducing the ease of their breathing.

The problems described above are primarily due to the geometry utilized in current sealing cushions. More specifically, traditional sealing flap/cushion designs consist of a seal interface in which the aperture primarily exists in a single plane from nose-bridge to upper lip area. In such designs, there is a small distance (0 to 10 mm) between the horizontal plane that intersects the nose bridge and the horizontal plane that intersects at the upper-lip area. This forces the sealing flap to contact the nose, cheeks, and upper lip at nearly the same time when donned by a patient. As a result, forces are applied to all these areas from the time of initial contact between the face and the mask. As force is applied to achieve a seal at the nose, cheeks, and upper lip, all of these areas will experience increasing compression from the time of initial contact until the time a seal is made. This causes undesired excessive force on those areas of an individuals' face which protrude out the furthest.

In addition, traditional sealing flap/cushion designs employ a large sealing surface area across and down onto the lip towards the mouth. This is again primarily due to the opening geometry of traditional sealing flap/cushion designs. In particular, the aperture's single plane opening results in a seal length at the upper lip area that is large. This is done to ensure sufficient sealing area across the nose bridge, while at the same time across and down the upper lip. As noted above, these traditional geometries require the nose and upper lip to contact the sealing interface at the same time, putting significant pressure on both areas of the face. Also, the sealing flap has to be far enough above any supporting cushion (integrated or not to the sealing flap) to ensure that there is a seal between the support geometry and the patient's upper lip. These constraints result in excessive flap length which consequently covers the majority of the patient's upper lip. This also often results in bunching of the sealing flap at the upper lip, which can reduce the quality of the seal and cause user discomfort and annoyance. Furthermore, the longer flap geometry of traditional designs as just described often results in the sealing flap riding up and partially occluding the airflow into the patient's nostrils (i.e., nostril encroachment), which typically makes breathing more difficult. Users may attempt to avoid this problem by wearing the masks further down on the upper lip. This, however, often results in additional contact area for lip pressure and discomfort to occur.

SUMMARY OF THE INVENTION

Accordingly, it is an object of the present invention to provide a cushion for a patient interface device that overcomes the shortcomings of conventional cushions. This object is achieved according to the present invention by providing cushion that includes an angled sealing flap providing an opening from the nose bridge to the upper lip that is created by two planes (hinged nearer the upper lip) that intersect at a large angle (e.g., 90 degrees to 150 degrees) near the upper lip.

In one embodiment, a cushion for a patient interface device is provided that includes a support wall portion and a sealing flap extending in inwardly from the support wall portion and toward a longitudinal axis of the cushion. The sealing flap has a distal edge which defines an opening in the sealing flap. The sealing flap also has an apex portion, a bottom portion located opposite the apex portion, a first side portion and a second side portion, wherein the bottom portion includes a first bottom section, a second bottom section and a third bottom section. The second bottom section and the third bottom section each extend from the first bottom section toward the apex portion, the first side portion extends from the second bottom section to a first side of the apex portion and the second side portion extends from the third bottom section to a second side of the apex portion. The distal edge of the sealing flap includes a first point located at a middle of the apex portion, a second point located at a junction of the second bottom section and the first side portion, a third point located at a junction of the third bottom section and the second side portion, a fourth point located at a junction of the second bottom section and the first bottom section, and a fifth point located at a junction of the third bottom section and the first bottom section, wherein the first point, the second point and the third point lie in a first plane, wherein the second point, the third point, the fourth point, and the fifth point lie in a second plane, and wherein an angle between the first plane and the second plane measured toward an interior of the cushion is greater than or equal to 90 degrees.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
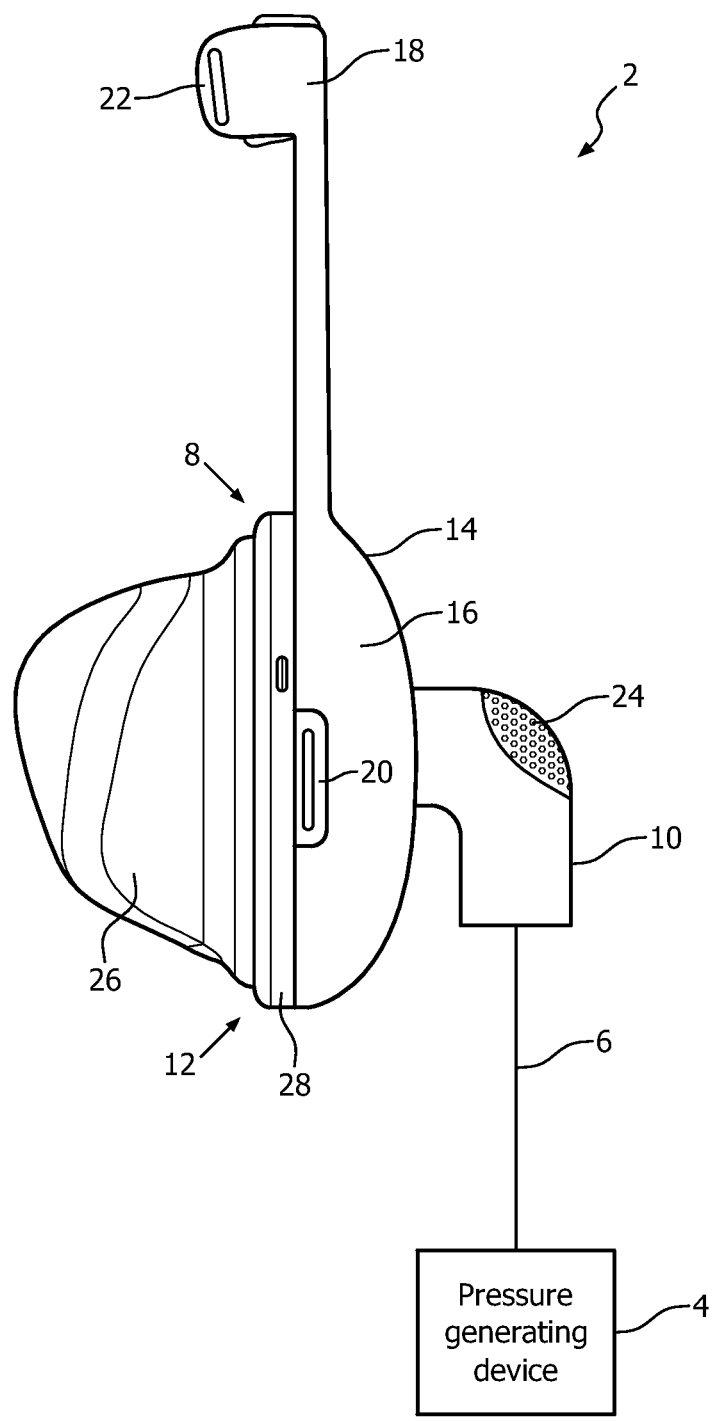
FIG. 1 is a schematic diagram of a system adapted to provide a regimen of respiratory therapy to a patient according to one exemplary embodiment of the invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

A system 2 adapted to provide a regimen of respiratory therapy to a patient according to one exemplary embodiment of the invention is generally shown in FIG. 1. System 2 includes a pressure generating device 4, a delivery conduit 6, and a patient interface device 8 including an elbow conduit 10. Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pennsylvania), and auto-titration pressure support devices. Delivery conduit 6 is structured to communicate the flow of breathing gas from pressure generating device 4 to patient interface device 8.

In the illustrated embodiment, patient interface device 8 comprises a nasal mask structured to cover the nose of the patient. In the embodiment shown in FIG. 1, patient interface device 8 includes a cushion assembly 12 and a frame member 14 having a faceplate portion 16 and a forehead support portion 18. Frame member 14 is made of a rigid or semi-rigid material, such as, without limitation, an injection molded thermoplastic or silicone. Straps (not shown) of a headgear component may be attached to faceplate portion 16 via attachment members 20 and to forehead support portion 18 via attachment members 22 to secure patient interface device 8 to the patient's head. An opening in faceplate portion 16 to which elbow conduit 10 is coupled allows the flow of breathing gas from pressure generating device 4 to be communicated to an interior space defined by faceplate portion 16 and cushion assembly 12, and then, to the airway of a patient. The opening in faceplate portion 16 also allows the flow of exhalation gas (from the airway of such a patient) to be communicated to exhaust vent 24 provided in elbow conduit 10.

Figure 2:
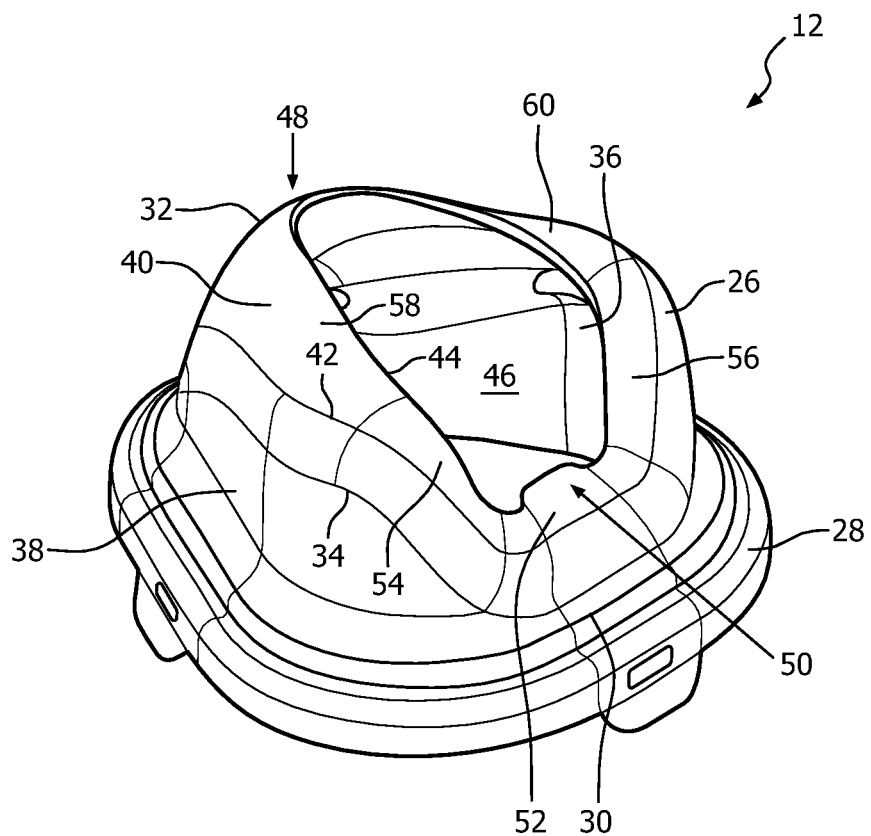
FIG. 2 is an isometric view.
Figure 3:
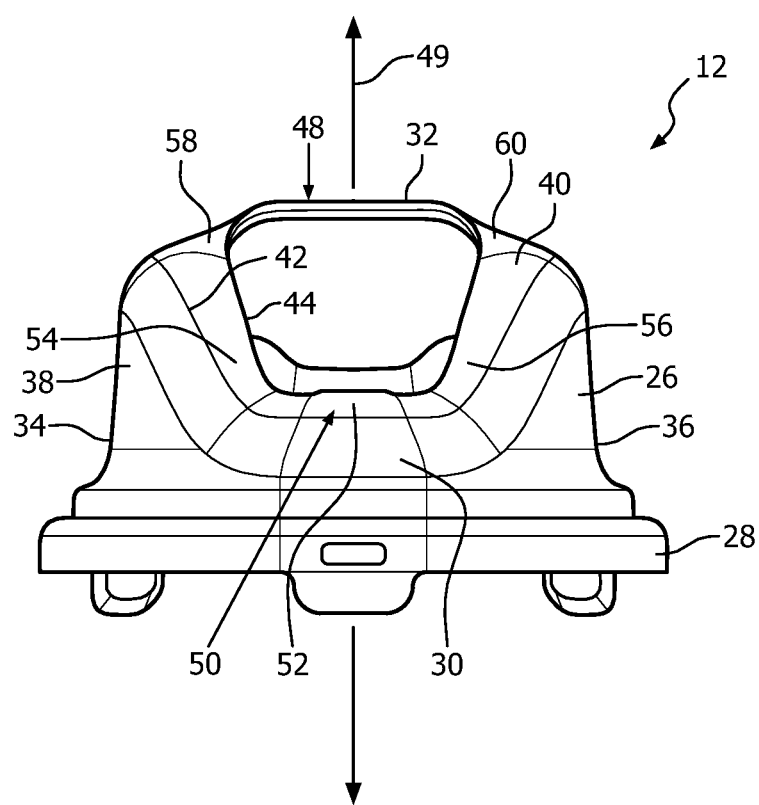
FIG. 3 is a rear elevational view.
Figure 4:
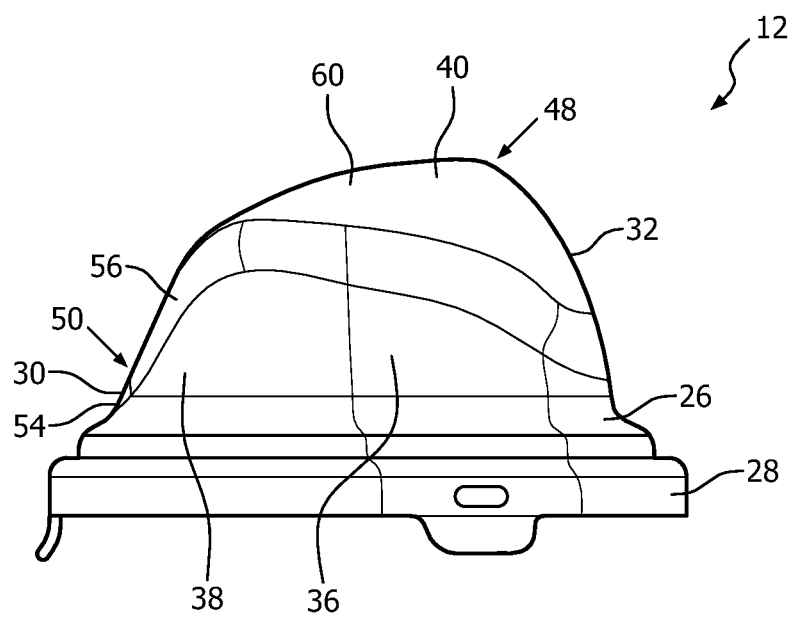
FIG. 4 is a side elevational view.
Figure 5:
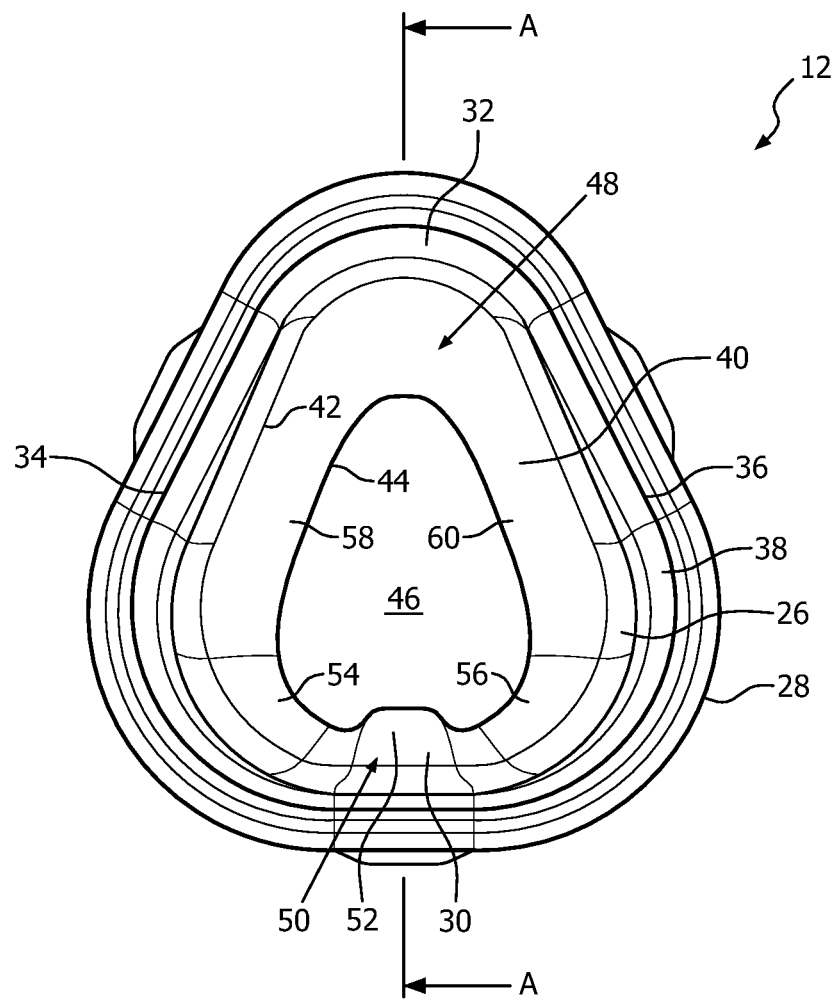
FIG. 5 is a top plan view.
Figure 6:
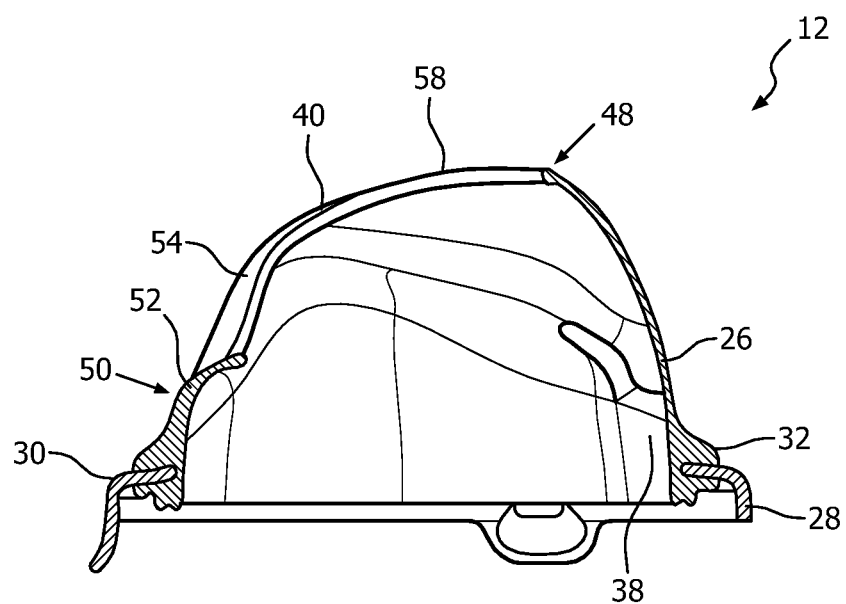
FIG. 6 is a cross-sectional view of a cushion assembly forming a part of a patient interface device of the system of FIG. 1.

FIG. 2 is an isometric view, FIG. 3 is a rear elevational view, FIG. 4 is a side elevational view, and FIG. 5 is a top plan view of cushion assembly 12 according to one non-limiting exemplary embodiment of the present in invention. FIG. 6 is a cross-sectional view of cushion assembly 12 taken along lines A-A of FIG. 5. Cushion assembly 12 includes a cushion member 26 coupled to a support ring 28. Support ring 28 is made from a rigid or semi-rigid material, such as, without limitation, an injection molded thermoplastic or silicone, and facilitates secure fluid connection of cushion assembly 12 to frame member 14.

In the exemplary embodiment, cushion member 26 is defined from a unitary piece of soft, flexible, cushiony, elastomeric material, such as, without limitation, silicone or an appropriately soft thermoplastic elastomer, or any combination of such materials. It will be understood, however, that cushion member 26 does not need to be unitary within the scope of the present invention. Rather, cushion member 26, and the parts thereof, may be made of separate components (e.g., separate sealing flap and support portion) that are coupled to one another by suitable means. In addition, as most readily seen in FIGS. 2 and 5, cushion assembly 12 has a generally triangular shape including a bottom region 30, an apex region 32 located opposite bottom region 30, a first side region 34 and a second side region 36 located opposite first side region 34. As a result, both cushion member 26 and support ring 28 will have associated bottom, apex and first and second side regions.

Cushion member 26 includes an outer wall 38 comprising a support portion of cushion member 26 and a sealing flap 40 that extends inwardly from outer wall 38. In the exemplary embodiment, outer wall 38 has a thickness of 1.5 to 8 mm (depending on durometer of utilized material), and sealing flap 40 has a thickness of 0.2 to 2 mm (depending on durometer of utilized material)[. As seen in FIGS. 2, 3 and 5, sealing flap 40 includes a proximal end 42 coupled to the top edge of outer wall 38 and a distal end 44 opposite proximal end 42, wherein distal end 44 defines a two-plane opening 46 (described in greater detail herein) structured to receive the patient's nose. Sealing flap 40 thus extends in a direction that is transverse to a longitudinal axis 49 (FIG. 3) of cushion assembly 12, wherein longitudinal axis 49 extends from the rear of cushion assembly 12 where cushion assembly 12 attaches to frame member 14 to the front of cushion assembly 12 (longitudinal axis 49 thus defines the general direction in which gasses flow through cushion assembly 12). In addition, in the exemplary embodiment, outer wall 38 extends outwardly from support ring 28 in a direction that is generally parallel to longitudinal axis 49 and generally perpendicular to the plane defining the rear of cushion assembly 12. Sealing flap 40 thus extends in an angled (e.g. upwardly or downwardly with respect to the plane just described; in the illustrated embodiment, it extend upwardly), cantilevered fashion from the top edge of outer wall 38 such that when patient interface device 8 is donned by the user, the user's face (e.g., the nose bridge, the cheeks (adjacent the alar base of the nose next to each nostril) and the area above the upper lip) will directly engage the top, outer surface of sealing flap 40 to form a seal therewith.

Sealing flap 40 includes an apex portion 48 and a bottom portion 50 located opposite apex portion 48. Bottom portion includes a first bottom section 52, a second bottom section 54 and a third bottom section 56. As seen in FIGS. 2 and 3, a length of first bottom section 52 extends in a direction that is generally parallel to a bottom-most edge of the cushion assembly 12 defined by support ring 28. Also, second bottom section 54 and third bottom section 56 both extend upwardly/outwardly from first bottom section 52 toward apex portion 48 such that first bottom section 52 is the part of sealing flap 40 that is located closest to sealing ring 28 along longitudinal axis 49 and closest to the bottom-most edge of the cushion assembly 12. Sealing flap 40 further includes a first side portion 58 that extends from an end of second bottom section 54 to a first side of apex portion 48, and a second side portion 60 that extends from an end of third bottom section 56 to a second, opposite side of apex portion 48.

Figure 7:
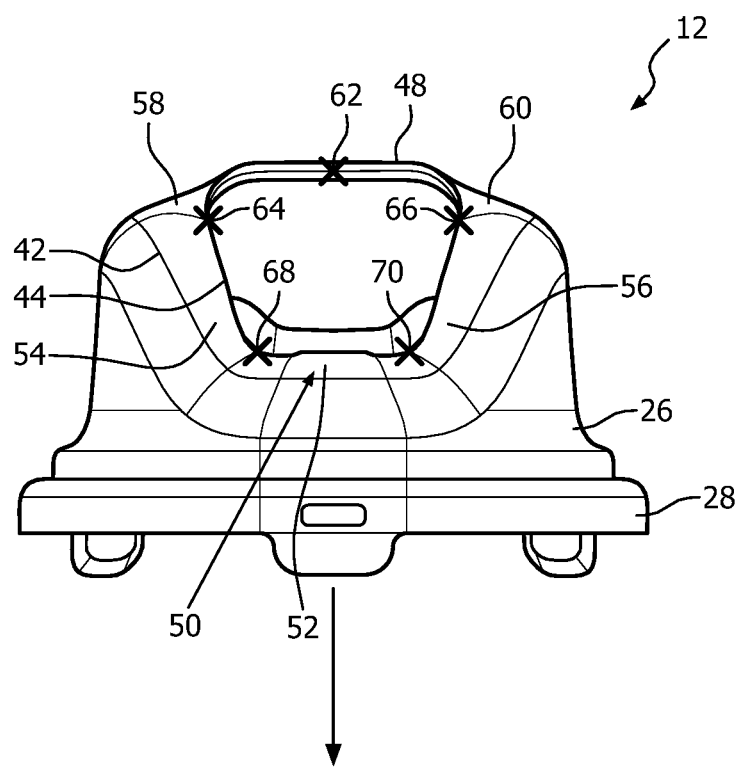
FIG. 7 is a rear elevational view of the cushion assembly of FIGS. 2-6 identifying certain particular points of the sealing flap thereof.

Referring to FIG. 7, a number of particular points (labeled with Xs in FIG. 7) on distal edge 44 of sealing flap 40 will now be described. Those points will then be used to describe the geometry of sealing flap 40 and opening 46 defined by the distal edge 44 of sealing flap 40. As seen in FIG. 7, distal edge 44 of sealing flap 40 includes a first point 62 located at the middle of apex portion 48, a second point 64 located at the junction of second bottom section 54 and first side portion 58, a third point 66 located at the junction of third bottom section 56 and second side portion 58, a fourth point 68 located at the junction of second bottom section 54 and first bottom section 52, and a fifth point 70 located at the junction of third bottom section 56 and first bottom section 52. When patient interface device 8 is donned by a user, first point 62 will engage the nose bridge of the user, second point 64 and third point 66 will engage opposite cheeks of the user (at an area adjacent the alar base of the nose next to each nostril), and fourth point 68 and fifth point 70 will engage opposite ends of the area above the upper lip of the user.

Figure 8:
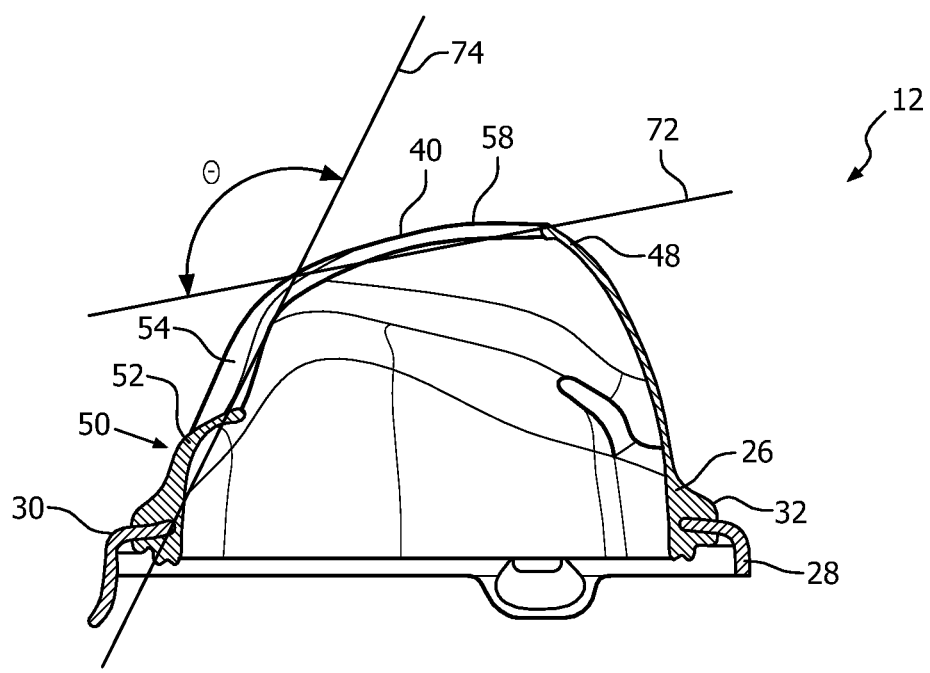
FIGS. 8 and 9 are cross-sectional views of the cushion assembly of FIGS. 2-6 illustrating the geometry of the opening in the sealing flap thereof

In addition, according to an aspect of the present invention, first point 62, second point 64 and third point 66 lie in a first plane defining a first part of opening 46. That first plane is shown in FIG. 8 and is labeled 72. Also, second point 64, third point 66, fourth point 68 and fifth point 70 lie in a second plane defining a second part of opening 46. That second plane is shown in FIG. 8 and is labeled 74. First plane 72 is transverse to second plane 74. According to an aspect of the present invention, the angle θ between first plane 72 and second plane 74 measured toward the interior of cushion member 26 is 90 degrees to 150 degrees. In an alternative embodiment, the angle 0 between first plane 72 and second plane 74 measured toward the interior of cushion member 26 is 105 degrees to 125 degrees to minimize flap length and pressure on the upper lip.

Figure 9:
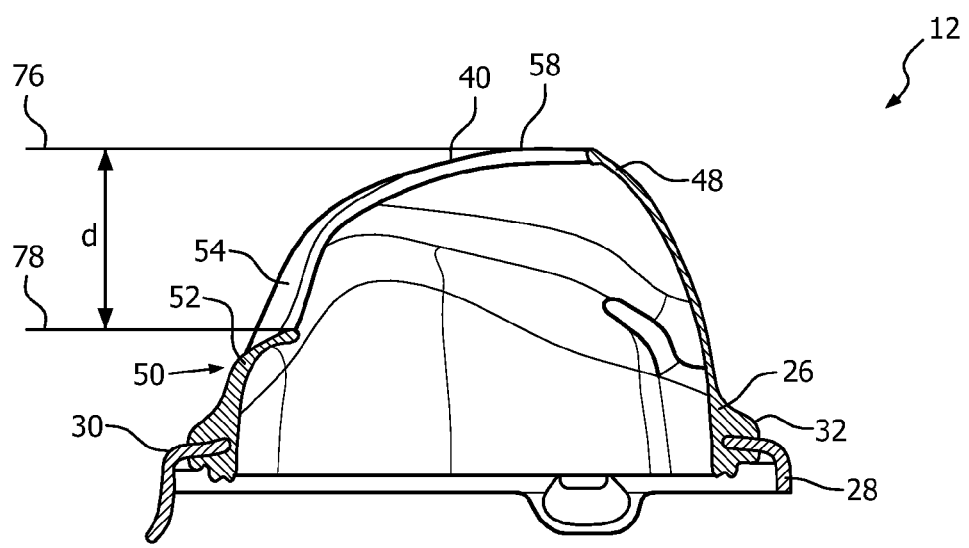

Moreover, referring to FIG. 9., in cushion member 26, a third plane 76 that includes first point 62 is perpendicular to longitudinal axis 49 and parallel to the plane defining the rear of cushion assembly 12, and a fourth plane 78 that includes fourth point 68 and fifth point 70 is perpendicular to longitudinal axis 49 and parallel to the plane defining the rear of cushion assembly 12. As seen in FIG. 9, third plane 76 and fourth plane 78 are parallel to one another and separated by a distance d. In the exemplary embodiment, the distance d is 15 mm to 30 mm. In an alternative embodiment, the distance d is 17 mm to 23 mm to minimize flap length and pressure on the upper lip.

Thus, as just described, the present invention provides an opening 46 from the nose bridge to the upper lip that is created by two planes 72, 74 (hinged nearer upper lip) that intersect at a large angle (90 degrees to 150 degrees) very near the upper lip. A distance (along an axis perpendicular to the longitudinal axis 49) from the middle of the bottom region of the sealing flap to the hinge of 8% to 28% of the total distance X (X=total length from the middle of the bottom region of the sealing flap to middle of the apex region of the sealing flap along an axis perpendicular to the longitudinal axis 49) may be utilized. In an alternative embodiment, a distance (along an axis perpendicular to the longitudinal axis 49) from the middle of the bottom region of the sealing flap to the hinge of 17% to 23% of the total distance X (X=total length from the middle of the bottom region of the sealing flap to middle of the apex region of the sealing flap along an axis perpendicular to the longitudinal axis 49) may be used to minimize flap length and pressure on the upper lip. This large angle allows a seal to occur with less pressure on the lip while distributing the strapping force further up the cushion at the cheek/alar base region of the face. These areas of the face are less sensitive to strapping force and sealing surface area effects than the upper lip.

When cushion member 26 is compressed against the face (negative z direction), sealing flap 40 as described herein will first press and conform into the nose bridge and sides of nose, will second press and conform into the cheek/alar base region, and will third press onto the upper lip for the final sealing area of the interface. This order of deflection and compression allows much of the strapping force to be absorbed into less sensitive areas than the upper lip. This results in a seal with less force on the upper lip area. The angle of sealing flap 40 and its order of deflection and compression also result in less sealing flap on and against the upper lip, as well as reducing the "bunching" of sealing flap 40 down the lip which occurs in traditional sealing flap designs. Sealing flap 40 also allows for a free and open air-path because the flap seal area is smaller and does not encroach over the nostrils and therefore increases ease of breathing.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A cushion for a patient interface device, comprising:
    a support wall portion; and
    a sealing flap extending inwardly from the support wall portion and toward a longitudinal axis of the cushion, the sealing flap having a distal edge which defines an opening in the sealing flap, the sealing flap having an apex portion, a bottom portion located opposite the apex portion, a first side portion and a second side portion, wherein the bottom portion includes a first bottom section, a second bottom section and a third bottom section, wherein the second bottom section and the third bottom section each extend from the first bottom section toward the apex portion, wherein the first side portion extends from the second bottom section to a first side of the apex portion and the second side portion extends from the third bottom section to a second side of the apex portion, wherein the distal edge of the sealing flap includes a first point located at a middle of the apex portion, a second point located at a junction of the second bottom section and the first side portion, a third point located at a junction of the third bottom section and the second side portion, a fourth point located at a junction of the second bottom section and the first bottom section, and a fifth point located at a junction of the third bottom section and the first bottom section, wherein the first point, the second point and the third point lie in a first plane, wherein the second point, the third point, the fourth point, and the fifth point lie in a second plane, wherein an angle between the first plane and the second plane measured toward an interior of the cushion is greater than or equal to 105 degrees and less than or equal to 125 degrees, and wherein the first point lies in a third plane that is perpendicular to the longitudinal axis and the fourth point and the fifth point lie a fourth plane that is parallel to the third plane, wherein the third plane and the fourth plane are separated by a distance that is greater than or equal to 15 mm and less than or equal to 30 mm, wherein the first plane and the second plane intersect at a hinge point, wherein a middle of the bottom portion and a middle of the apex portion are separated by a first distance measured along an axis perpendicular to the longitudinal axis, wherein the middle of the bottom portion and the hinge point are separated by a second distance measured along the axis perpendicular to the longitudinal axis, and wherein the second distance is 8% to 28% of the first distance.

2. The cushion according to claim 1, wherein the distance separating the third plane and the fourth plane is greater than or equal to 17 mm and less than or equal to 23 mm.

3. The cushion according to claim 1, wherein the cushion is a nasal cushion structured to cover a nose of a user.

4. The cushion according to claim 3, wherein the first point is structured to engage a nose bridge of the user, the second point and the third point are structured to engage opposite cheeks of the user, and the fourth point and the fifth point are structured to engage opposite ends of an area above an upper lip of the user when the patient interface device is donned by the user.

5. The cushion according to claim 1, wherein the support wall portion and the sealing flap are part of a unitary structure.

6. The cushion according to claim 1, wherein the first bottom section is located closer to a rear of the cushion along the longitudinal axis than the apex portion, the first side portion and the second side portion.

7. A cushion assembly including a support ring and a cushion according to claim 1 coupled to the support ring.

8. A patient interface device including a cushion according to claim 1.

9. A system for delivering a flow of breathing gas to a patient, comprising a pressure generating system structured to generate the flow of breathing gas and a patient interface device fluidly coupled to the pressure generating system, wherein the patient interface device includes a cushion according to claim 1.

10. The cushion according to claim 1, wherein the second distance is 17% to 23% of the first distance.

* * * * *